United States Patent
Choi et al.

(10) Patent No.: US 12,188,683 B2
(45) Date of Patent: Jan. 7, 2025

(54) MACHINE LEARNING-BASED AIR HANDLER AND CONTROL METHOD THEREOF

(71) Applicant: AweXome Ray, Inc., Gyeonggi-do (KR)

(72) Inventors: Hong Soo Choi, Seoul (KR); Jun Young Choi, Gyeonggi-do (KR); Sung Hyun Bae, Seoul (KR); Nam Kyu Lee, Gyeonggi-do (KR); Gi Hoon Yoon, Seoul (KR); Chang Hyun Kim, Gyeonggi-do (KR); Se Hoon Gihm, Seongnam-Si (KR)

(73) Assignee: AweXome Ray, Inc., Anyang-si (KR)

( * ) Notice: Subject to any disclaimer, the term of this patent is extended or adjusted under 35 U.S.C. 154(b) by 510 days.

(21) Appl. No.: 17/360,030

(22) Filed: Jun. 28, 2021

(65) Prior Publication Data

US 2022/0003440 A1    Jan. 6, 2022

(30) Foreign Application Priority Data

Jun. 29, 2020   (KR) .................. 10-2020-0079472
Jan. 21, 2021   (KR) .................. 10-2021-0008668

(51) Int. Cl.
| | |
|---|---|
| *A61L 9/22* | (2006.01) |
| *B01D 53/14* | (2006.01) |
| *B03C 3/38* | (2006.01) |
| *F24F 8/10* | (2021.01) |
| *G06N 20/00* | (2019.01) |

(52) U.S. Cl.
CPC .................. *F24F 8/10* (2021.01); *A61L 9/22* (2013.01); *B01D 53/1487* (2013.01); *B03C 3/38* (2013.01); *G06N 20/00* (2019.01); *B01D 2257/708* (2013.01); *B01D 2258/06* (2013.01)

(58) Field of Classification Search
CPC .. F24F 11/00; F24F 11/62; F24F 7/003; F24F 8/00; G05B 13/02; G05B 13/04; G06N 3/04

See application file for complete search history.

(56) References Cited

U.S. PATENT DOCUMENTS 11,408,629 B2 *   8/2022   Lee .................... F24F 11/62

FOREIGN PATENT DOCUMENTS

| CN | 202460841 U | 10/2012 |
| CN | 105170333 A | 12/2015 |
| CN | 106895551 B | 5/2019 |

(Continued)

OTHER PUBLICATIONS

KR20190106929 (Year: 2019).*

(Continued)

*Primary Examiner* — Sharon Pregler (74) *Attorney, Agent, or Firm* — Young Basile Hanlon & MacFarlane, P.C.

(57) ABSTRACT

Disclosed is a machine learning-based air handler and a control method thereof, the control method including collecting first data on an air quality of air flowing into the air handler, controlling a purification part based on the first data, collecting second data on an air quality of air passing through the purification part, and controlling the purification part according to a machine-learning model generated based on a setting value related to a control of the purification part, the first data, and the second data.

12 Claims, 5 Drawing Sheets

(56) References Cited

FOREIGN PATENT DOCUMENTS

| KR | 10-2012-0009533 A | 2/2012 |
|---|---|---|
| KR | 101261198 B1 | 5/2013 |
| KR | 101322886 B1 | 10/2013 |
| KR | 101591735 B1 | 2/2016 |
| KR | 10-2017-0078372 A | 7/2017 |
| KR | 101757446 B1 | 7/2017 |
| KR | 10-1970705 B1 | 5/2018 |
| KR | 10-2019-0026546 A | 3/2019 |
| KR | 10-2019-0096310 A | 8/2019 |
| KR | 20190106929 * | 9/2019 |
| KR | 10-2020-0067380 A | 6/2020 |
| WO | 2020078008 A1 | 4/2020 |

OTHER PUBLICATIONS

Decision to Grant issued in co-pending application KR 10-2021-0008668 mailing date: Sep. 8, 2021 (4 pages).
International Search Report for co-pending application PCT/KR2021/008076 mailed Sep. 24, 2021 (4 pages).
Office Action issued Mar. 4, 2022 in co-pending TW Application No. 110123835 (11 pages).
Application for examination/priority examination for co-pending application KR10-2021-0008668 with machine English translation.
Office Action in co-pending application KR 10-2021-0008668 mailed Apr. 28, 2021 with machine English translation.
Supplementary European Search Report issued in co-pending Application No. EP 21 83 2713 dated Sep. 6, 2024 (54 pages).

* cited by examiner

MACHINE LEARNING-BASED AIR HANDLER AND CONTROL METHOD THEREOF

The subject invention was developed with funding from the Korean Environmental Industry & Technology Institute (KEITI)'s National Research & Development (R&D) Project; the names of these R&D projects are "Commercialization of Smart Ventilation System for Green Remodeling and Wellness Value Added" (project No. 2020003170004) and "Technology Development for Improvement and Use Diversification of Smart Ventilation System" (project No. 2020003160003).

FIELD

The present disclosure relates to a machine learning-based air handler and a control method thereof. More specifically, the present disclosure relates to an air handler that measures an air quality before and after air passes through a purification part purifying the air and perform machine-learning using a setting value related to a control of the purification part, thereby achieving an optimal air purification efficiency based on a space in which the air handler is installed, and a control method of the air handler.

BACKGROUND

In general, an air handler in a large office building purifies air by filtering and pollutants floating in the air using a high efficiency particulate air (HEPA) filter circulating the air. However, when the typical air handler using the HEPA filter is used for a long time, pores between the filters are clogged by fine dust, resulting in differential pressure and vibration, so the ability to filter fine dust is also reduced.

To solve this, an electrostatic precipitator for removing pollutants without differential pressure may be considered. The electrostatic precipitator is a device that is installed in an air handler such as an air purifier, air conditioner, or heater to collect dust by charging foreign substances such as dust in the air. The electrostatic precipitator may include a charging part including a discharging device generating an electric field, and a dust collecting part in which pollutant particles charged by the charging part are collected. After the air passes through the charging part, pollutants in the air may be collected in the dust collecting part while passing through the dust collecting part. For this, if a high voltage of several thousand volts is applied to the charged part, electrons are generated from the electrode itself or from the gas around the electrode to form plasma around the electrode. When the electrons are separated from atoms or molecules in a gaseous state by the plasma and attached to particles in the air, the particles are charged with a negative charge. The negatively charged dust particles may be removed by moving and clinging to a positively charged dust collecting plate by electrostatic attraction.

However, such electrostatic precipitation method may generate oxides such as ozone or nitrogen oxides in an air purification process. Because these oxides are highly reactive, they exhibit a sterilizing effect that promotes the decomposition of harmful substances in the air but may increase the ozone concentration indoors, which can be dangerous to the human body. For example, when a person is exposed to ozone, it can cause eye irritation or damage to the bronchial tubes. Also, since such electrostatic precipitation method requires a high voltage, it requires high facility and operating costs, and there is a risk of explosion in an environment with high dust density.

In addition, a typical electrostatic precipitation method used for air conditioning generates ions having a negative charge and charges air pollutant substances combined thereto with the negative charge. Therefore, it is possible to collect particles of the pollutant substances from the dust collecting plate having a positive charge, but it is difficult to collect the particles from a dust collecting plate having a negative charge. This may reduce a dust collection efficiency. Also, if the negatively charged substance is not collected in the dust collecting plate and is recovered in the air again, the negative ions in the air become excessive, which may break the ion balance and cause further generation of oxides.

Moreover, in the typical electrostatic precipitation method, unnecessary power is wasted because the air handler operates on the same basis regardless of the characteristics of the space where the air handler is installed. However, even if the air handler of the same product is installed in the same building, air characteristics such as a temperature, a humidity, an amount of fine dust, carbon dioxide, volatile organic compounds (VOCs), formaldehyde, and the like may be different depending on the area in the building. Thus, an operation condition for each air handler needs to be optimized. Alternatively, for example, even if the same air handler is installed in an underground station, the quality of the air in the platform may vary each time zone, so it is necessary to operate the air handler to purify the air with minimum power consumption.

SUMMARY

Technical Goals

To solve the above-described issues, an aspect of the present disclosure provides an air handler that does not generate ozone, which is a harmful substance, as a byproduct that ionizes pollutants in the air, and a control method thereof.

Further, another aspect of the present disclosure provides a machine learning-based air handler that derives a purification part operation condition optimized for a space in which the air handler is installed to control a purification part of the air handler according to the purification part operation condition, and a control method thereof.

The goals to be achieved by example embodiments of the present disclosure are not limited to the objectives described above and other objects may be inferred from the following example embodiments.

Technical Solutions

According to an aspect, there is provided a method of controlling a machine learning-based air handler, the method including collecting first data on an air quality of air flowing into the air handler, controlling a purification part based on the first data, collecting second data on an air quality of air passing through the purification part, and controlling the purification part according to a machine-learning model generated based on a setting value related to a control of the purification part, the first data, and the second data.

According to another aspect, there is also provided a machine learning-based air handler including a purification part, a first data collector including at least one sensor and configured to acquire information associated with air flowing into the purification part, a second data collector including at least one sensor and configured to acquire information associated with air discharged from the purification part, and a controller, wherein the controller is configured to collect first data on an air quality acquired through the first data collector, control the purification part based on the first data, collect, through the second data collector, second data on an air quality of air passing through the purification part, and control the purification part according to a machine-learning model generated based on a setting value related to a control of the purification part, the first data, and the second data.

Effects

According to example embodiments, since pollutants in the air are ionized using an electromagnetic wave having a wavelength of low energy, a differential pressure may not be applied before and after the air passes through an air handler, and no or little ozone may be generated.

Further, according to example embodiments, in a charging part of the present disclosure, it is possible to charge pollutant substances in the air with a positive charge as well as a negative charge. As such, pollutant particles may be collected at both positively charged dust collecting plate and negatively charged dust collecting plate, thereby achieving the dust collecting efficiency. In addition, even if some of the charged pollutant substances pass through a dust collecting part without being collected, the balance of ions in the air may be maintained because negatively charged substances and positively charged substances are balanced.

Further, according to example embodiments, since a voltage applied to a purification part is set through machine learning based on a space in which an air handler is installed, a space-customized design is possible. Also, power consumption of the air handler may be minimized through the machine learning, which may increase an efficiency of removing pollutant substances per power usage.

Effects of the present disclosure are not limited to those described above and other effects may be made apparent to those skilled in the art from the following description.

BRIEF DESCRIPTION OF THE DRAWINGS

FIG. 3 is a diagram illustrating a purification part 220 according to an example embodiment.

DETAILED DESCRIPTION

Hereinafter, example embodiments of the present disclosure will be described in detail with reference to the drawings.

In describing the example embodiments, descriptions of technical contents that are well known in the art to which the present disclosure belongs and are not directly related to the present specification will be omitted. This is to more clearly communicate without obscure the subject matter of the present specification by omitting unnecessary description.

For the same reason, in the accompanying drawings, some components are exaggerated, omitted or schematically illustrated. In addition, the size of each component does not fully reflect the actual size. The same or corresponding components in each drawing are given the same reference numerals.

Advantages and features of the present disclosure and methods of achieving them will be apparent from the following example embodiments that will be described in more detail with reference to the accompanying drawings. It should be noted, however, that the present disclosure is not limited to the following example embodiments, and may be implemented in various forms. Accordingly, the example embodiments are provided only to disclose the present disclosure and let those skilled in the art know the category of the present disclosure. In the drawings, embodiments of the present disclosure are not limited to the specific examples provided herein and are exaggerated for clarity. The same reference numerals or the same reference designators denote the same elements throughout the specification.

At this point, it will be understood that each block of the flowchart illustrations and combinations of flowchart illustrations may be performed by computer program instructions. Since these computer program instructions may be mounted on a processor of a general-purpose computer, special purpose computer, or other programmable data processing equipment, those instructions executed through the computer or the processor of other programmable data processing equipment may create a means to perform the functions be described in flowchart block(s). These computer program instructions may be stored in a computer usable or computer readable memory that can be directed to a computer or other programmable data processing equipment to implement functionality in a particular manner, and thus the computer usable or computer readable memory. It is also possible for the instructions stored in to produce an article of manufacture containing instruction means for performing the functions described in the flowchart block(s). Computer program instructions may also be mounted on a computer or other programmable data processing equipment, such that a series of operating steps may be performed on the computer or other programmable data processing equipment to create a computer-implemented process to create a computer or other programmable data. Instructions for performing the processing equipment may also provide steps for performing the functions described in the flowchart block(s).

In addition, each block may represent a portion of a module, segment, or code that includes one or more executable instructions for executing a specified logical function(s). It should also be noted that in some alternative implementations, the functions noted in the blocks may occur out of order. For example, the two blocks shown in succession may in fact be executed substantially concurrently, or the blocks may sometimes be executed in the reverse order, depending on the corresponding function.

According to various embodiments of the present disclosure, the term " . . . part", means, but is not limited to, a software or hardware component, such as a Field Programmable Gate Array (FPGA) or Application Specific Integrated Circuit (ASIC), which performs certain tasks. " . . . part" may advantageously be configured to reside on the addressable storage medium and be configured to be executed on one or more processors. Thus, " . . . part" may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and " . . . parts" may be combined into fewer components and " . . . parts" or further separated into additional components and " . . . parts". In addition, the components and " . . . parts" may be implemented such that they execute one or more CPUs in a device or a secure multimedia card.

The air handler of the present disclosure is for controlling air and may include an air purifier for performing an air purifying operation.

Figure 1:
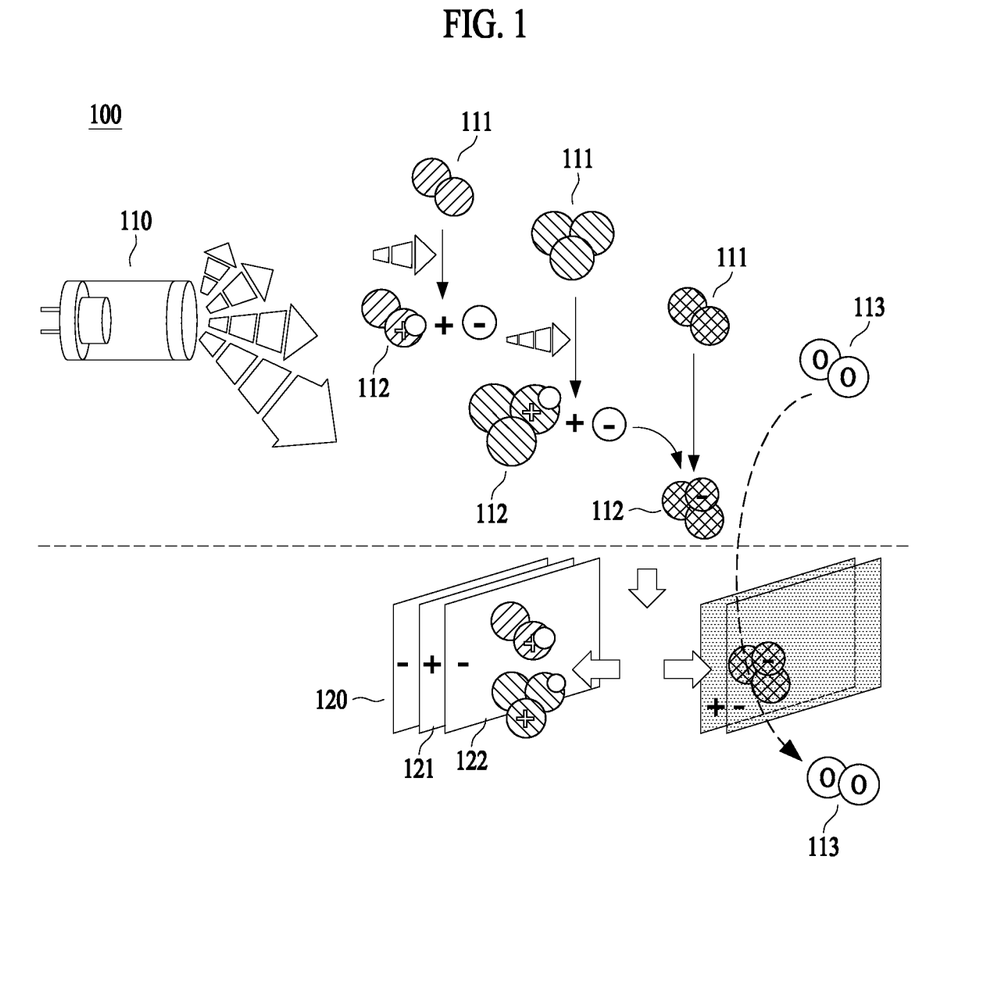
FIG. 1 is a diagram illustrating an air purifying operation of a purification part of an air handler according to an example embodiment.

FIG. 1 is a diagram illustrating an air purifying operation of a purification part of an air handler according to an example embodiment.

An air handler of the present disclosure includes a purification part 100. The purification part 100 may include a charging part 100 that ionizes at least a portion of substances included in air and a dust collecting part 120 that collects ionized substances.

Similar to an electrostatic precipitator using a typical photoionization method, the purification part 100 of the present disclosure ionizes particles and molecules of pollutants in the air in the charging part 110 and then collects the ionized particles and molecules in the dust collecting part 120. Specifically, the purification part 100 may apply a voltage to the charging part 110 to ionize pollutants 111 and collect ionized pollutants 112 on dust collecting plates 121 and 122 of the dust collecting part 120. According to an example embodiment, the charging part 110 of the present disclosure uses an electromagnetic wave of a low energy wavelength, so ozone is hardly generated. Also, the charging part 110 may charge pollutants in the air with negative charges as well as positive charges using a low wavelength of electromagnetic wave which has low energy, so that pollutant particles can be collected at both positively charged plate and negatively charged plate. Accordingly, pollutants 112 having negative charges may move to and be collected at a positively charged collecting plate 121 by electrostatic attraction. Also, the pollutants 112 having positive charges may move to and be collected at a negatively charged collecting plate 122. Meanwhile, a clean gas 113 such as oxygen, which is not a pollutant in the air, is not ionized by the charging part 110 and does not have a specific charge. Thus, the clean gas 113 may pass without being collected in the dust collecting part 120. As such, using the purification part 100 of the present disclosure, it is possible to ionize and collect only pollutant substances. The pollutant substances may be, for example, fine dust, volatile organic compounds (VOCs), and formaldehyde.

Meanwhile, because a high voltage of 8 to 15 kilovolts (kV) is applied to a charging part using a typical electrostatic precipitation method, plasma is formed around an electrode. Due to this, even oxygen, which is not a pollutant, may be ionized, and ozone may be generated as a byproduct. In contrast, the charging part 110 of the present disclosure uses an electromagnetic wave having a wavelength in a relatively low energy range and thus, may apply a voltage of 5 kV or less. Therefore, no plasma may be generated, and no or little amount of ozone may be generated. The charging part 110 according to an example embodiment of the present disclosure may ionize a substance using an electromagnetic wave having a wavelength of a range between 0.1 nanometers (nm) and 100 nm, inclusive. Specifically, the charging part 110 may use extreme ultraviolet (EUV) having a wavelength of 13.5 nm or a soft X-ray having a wavelength of a range between 0.1 nm and 10 nm, inclusive. In a case of using an electromagnetic wave having a wavelength of a low energy range, such as extreme ultraviolet or soft X-ray, a differential pressure and ozone may not be generated. Thus, it is possible to install the purification part 100 of the present disclosure in an existing air handler and achieve a high by-pass performance. For example, the extreme ultraviolet may have a by-pass performance of 50%, and the soft X-ray may have a by-pass performance of 75%.

Figure 2:
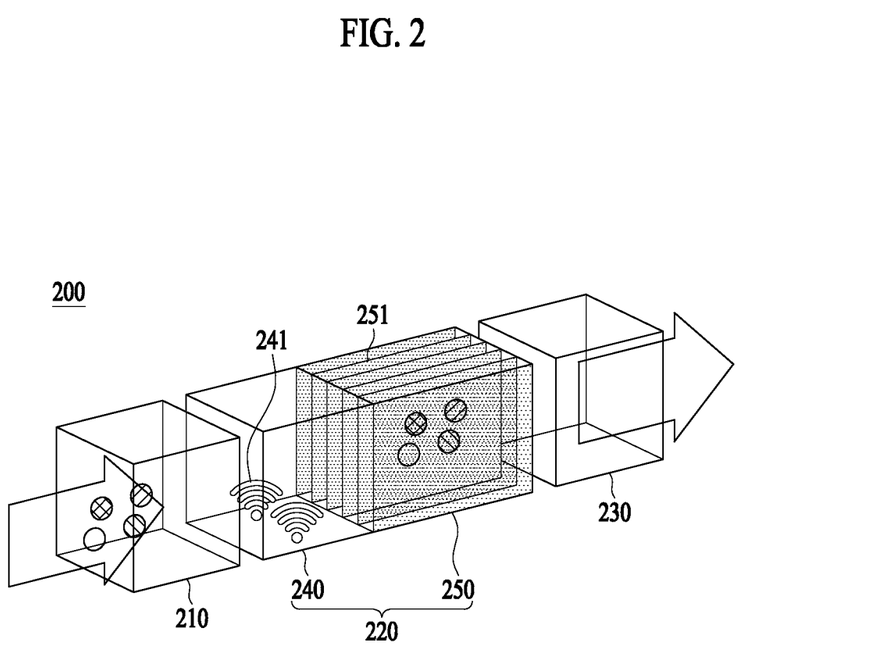
FIG. 2 is a diagram illustrating an air handler according to an example embodiment.

FIG. 2 is a diagram illustrating an air handler according to an example embodiment.

An air handler 200 according to the present disclosure may include a purification part 220 to purify air, a first data collector 210 to acquire information associated with air flowing into the purification part 220, and a second data collector 230 to acquire information associated with air discharged from the purification part 220. Each of the first data collector 210 and the second data collector 230 may include at least one sensor to collect data on an air quality.

The purification part 220 according to an example embodiment may include at least one charging part 240 to ionize at least a portion of substances included in the air and include a dust collecting part 250 to collect substances ionized in the charging part 240. The charging part 240 may include at least one tube 241 to emit an electromagnetic wave. According to an example embodiment, the tube 241 may be an X-ray tube that generates an X-ray through a collision between a metal target and an electron and may include an anode and a cathode. The tube 241 may further include a gate electrode as necessary. Here, the cathode that emits an electric field may include a field emitting element that is composed of a carbon nanotube (CNT) and emits a soft X-ray having a wavelength between 0.1 nm and 10 nm, inclusive. In this case, the field emitting element, for example, an emitter of the cathode may include a CNT structure including a plurality of unit yarns of a structure in which a plurality of CNTs is aggregated and extended in a first direction. According to an example embodiment, the charging part 240 may ionize substances using an electromagnetic wave having a wavelength of a range between 0.1 nm and 100 nm, inclusive. For example, the charging part 240 may photo-ionize pollutant substances using extreme ultraviolet or soft X-rays. The dust collecting part 250 may include at least one dust collecting plate 251 to collect ionized substances.

The air handler 200 according to the present disclosure may collect first data on an air quality of air flowing into the air handler 200 through the first data collector 210. The first data may include at least one of information on an air pollutant such as fine dust, VOCs, and formaldehyde, carbon dioxide, a wind speed, a temperature, a humidity, and a size of a space in which the air handler 200 is installed, and may include all information associated with the air quality. The information on the fine dust may include a concentration of the fine dust and a concentration of ultrafine dust. The air may pass through the purification part 220. In this instance, the purification part 220 may be controlled based on the collected first data. For example, the air handler 200 may be set to operate when, among parameters related to the air quality, a concentration of fine dust is 75 microgram per cubic meter ($\mu g/m^3$) or more and a concentration of ultrafine dust is 30 $\mu g/m^3$ or more in the air. In this example, when a concentration of fine dust in the air according to the first data collected in the first data collector 210 is 80 $\mu g/m^3$, the air handler 200 may operate.

According to an example embodiment, after the air passes through the purification part 220, the second data collector 230 may collect second data on the air quality of air. The second data may include at least one of information on an air pollutant such as fine dust, VOCs, and formaldehyde, carbon dioxide, a wind speed, a temperature, a humidity, and a size of a space in which the air handler 200 is installed, and may include all information associated with the air quality. Once the air passes through the purification part 220, a value indicated in the second data may be a value improved compared to a value indicated in the first data.

The air handler 200 according to the present disclosure may generate a model by performing machine learning based on a setting value related to a control of the purification part 220, the first data measured in the first data collector 210, and the second data measured in the second data collector 230 and control the purification part 220 according to the generated model. In this instance, the control of the purification part 220 may indicate controlling a voltage applied to the charging part 240 and a voltage applied to the dust collecting part 250. The voltage applied to the charging part 240 may correspond to a voltage applied to the tube 241. According to an example embodiment, the tube 241 may include a carbon nanotube. Also, controlling the voltage applied to the charging part 240 may include an individual control of a voltage applied to the anode, the cathode, or a gate of the tube 241. The air handler 200 may be driven based on an initial value before the machine learning is performed. The initial value may be previously set based on a minimum air quality that satisfies the law of indoor air quality management.

The air handler 200 according to the present disclosure may control the purification part 220 to perform an operation customized for a space in which the air handler 200 is installed. To this end, the air handler 200 may derive a threshold based on the first data and the second data on the air quality of the air passing through the purification part 220. According to an example embodiment, the second data may be data on the air quality of the air passing through the purification part 220 set according to the initial value or the setting value related to the control of the purification part 220, which is derived through the machine-learning model. The threshold may be a threshold for a parameter related to the air quality. The parameter may include at least one of information on an air pollutant such as fine dust, VOCs, and formaldehyde, carbon dioxide, a wind speed, a temperature, a humidity, and a size of a space in which the air handler 200 installed. Also, the threshold may be different for each space in which the air handler 200 is installed. In an example, when the air handler 200 is installed in two spaces, a vehicle that is periodically ventilated and a closed underground station, the two places may have different air quality data and thus, may have different control conditions of the purification part 220. For example, since the underground station is an enclosed space, the threshold may be set to be relatively low, so that the air purification is frequently performed. In addition, the threshold may be determined based on a size of fine dust included in the second data. For example, when a particle size of the fine dust is less than or equal to 10 micrometers (μm) (e.g., PM 10), a criterion applied to the fine dust may be applied. Also, when a particle size of the fine dust is less than or equal to 2.5 μm (e.g., PM 2.5), a criterion applied to the ultrafine dust may be applied.

According to an example embodiment, the air handler 200 may derive a control condition of the purification part 220 such that the parameter reaches the threshold or more or less. Such control condition of the purification part 220 may include a voltage applied to the charging part 240 and a voltage applied to the dust collecting part 250. The voltage applied to the charging part 240 may correspond to the voltage applied to the tube 241. According to an example embodiment, the tube 241 may include a carbon nanotube. Also, controlling the voltage applied to the charging part 240 may include an individual control of a voltage applied to the anode, the cathode, or the gate of the tube 241.

Meanwhile, the number of the tubes 241 used in the charging part 240, a location of the tube 241, and a size of the dust collecting part 250 (or a dust collecting plate 251) and the like may vary based on product characteristics of the air handler 200. According to this, the air handler 200 may previously input the number of at least one tube 241 that emits an electromagnetic wave in the charging part 240, a location of the at least one tube 241, and a size of the dust collecting part 250 before machine learning for controlling the purification part 220 is performed.

According to an example embodiment, the air handler 200 of the present disclosure may continuously update the machine-learning model even after operating the purification part 220 by deriving the control condition of the purification part 220 through the machine learning. The machine learning may be continually performed using a data set including the first data and the second data acquired while the purification part 220 is normally operated according to the control condition derived through the machine learning. When the air quality is improved even under the same control condition so that the air can be purified with less power consumption, an optimal threshold that reduces the voltage supplied to the purification part 220 while maintaining the air purification may be derived. When the air quality deteriorates under the same control condition, the air handler 200 may continue to run to adjust an air quality parameter below or above the threshold. In this case as well, the machine learning may be continually performed using a data set including the first data and the second data acquired while the purification part 220 is normally operated. The air handler 200 according to an example embodiment may collect the first data and the second data for the machine learning for a preset period of time in predetermined time units. For example, the air handler 200 may build a data set by collecting the first data and the second data for one week in units of five seconds.

According to an example embodiment, the air handler 200 of the present disclosure may generate a machine-learning model through reinforcement learning in which compensation is performed based on the parameter related to the air quality and the power consumption of the purification part 220. Specifically, voltages of the charging part 240 and the dust collecting part 250 may be randomly selected at intervals of a preset period of time within a range derived through the machine learning, and the first data and the second data may be collected accordingly. Also, the reinforcement learning may be performed by assigning a score such that the power consumption of the air handler 200 is reduced while the parameter related to the air quality satisfies the threshold. For example, as initial conditions, a range of voltage applied to the charging part 240 may be set to a range of 4.0 to 4.8 kV, and a range of voltage applied to the dust collecting part 250 may be set to a range of 2.8 to 4.4 kV. In this example, air quality data of air before and after the air passes through the purification part 220 may be collected by randomly selecting each partial voltage at intervals of 20 seconds within a preset range of voltage. As a result of the reinforcement learning, an efficiency of removing the fine dust compared to the power consumption may be maximized when the voltage applied to the charging part 240 is 4.3 kV and the voltage applied to the dust collecting part 250 is 3.5 kV. Accordingly, thresholds may be set to be 4.3 kV and 3.5 kV. According to an example embodiment, the charging part 240 may include a plurality of tubes 241. In this case, voltages applied to the respective tubes 241 may be slightly different. Thus, an average value may be obtained for the respective tubes 241 and reflected as the voltage of the charging part 240. Alternatively, when a plurality of charging parts 240 is present in the purification part 220, instead of performing the machine learning on each of the charging parts 240, the machine learning may be performed by applying the same value of voltage to the charging parts 240. For this, the number of charging parts 240 or the number of tubes 241 may be input before first machine learning is performed so as to be reflected in the machine learning.

Meanwhile, the machine-learning model may be generated through the reinforcement learning, and other machine learning algorithms may also be used to generate a model applied to the air handler 200 of the present disclosure. For example, various machine learning algorithms such as an unsupervised learning algorithm, a rule-based machine learning algorithm, and the like may apply to the present disclosure.

FIG. 3 is a diagram illustrating a purification part 220 according to an example embodiment. Referring to FIG. 3, the purification part 220 may include a plurality of charging parts, for example, a first charging part 240-1 and a second charging part 240-2 and the dust collecting part 250. Each of the charging parts 240-1 and 240-2 may be a module that ionizes pollutant substances in the air. A setting value according to machine learning may be equally applied to the first charging part 240-1 and the second charging part 240-2, or voltage values having a neglectable difference therebetween may be applied to the first charging part 240-1 and the second charging part 240-2.

Meanwhile, because air quality data changes based on locations of sensors of the first data collector 210 and the second data collector 230, the control condition of the purification part 220 derived using a model trained based on the first data and the second data may also be changed. Accordingly, the locations of the sensors of the first data collector 210 and the second data collector 230 may be changed based on a structure, air quality characteristics, and the like of a space in which the air handler 200 is installed.

According to an example embodiment, a plurality of air handlers 200 may be installed in the same space. In this case, according to different machine learning models, the air handlers 200 may control purification parts 220 therein. That is, for each of the air handlers 200, a threshold applied to an air quality parameter may be different.

When compared to a typical electrostatic precipitator using a corona discharge method, the air handler 200 of the present disclosure may have a high dust collection efficiency compared to the power consumption so a resulting ozone generation converges to zero. For example, a typical electrostatic precipitator may consume 110 watts (W) of power, have 10% of the dust collection efficiency compared to ionization, and generates approximately 65 parts per million (ppm) of ozone. In this case, the air handler of the present disclosure may consume 40 W of power, have 50% of the dust collection efficiency compared to ionization, and generates approximately 0 ppm of ozone.

The air handler 200 of the present disclosure may derive an optimal operation condition according to an environment and a space in which the air handler is installed and thus, may minimize energy consumption. In addition, since the machine learning is used, system configuration may not be possible unless a digital generating device capable of controlling energy in real time is provided. For this reason, it is difficult to configure the air handler 200 of the present disclosure using a typical ultraviolet or X-ray hot cathode tube. Instead, a carbon nanotube, which generates an electromagnetic wave using a relatively low energy and is easy to control energy, may be used to configure the air handler 200 of the present disclosure.

For example, a thermionic emission tube such as a typical ultraviolet or X-ray hot cathode tube may include a negative electrode made of a metal filament and a positive electrode that is a metal target, and may use a principle that electrons are emitted from a heated metal filament (negative electrode). That is, the metal filament of the thermionic emission tube may be heated to 1000 degrees Celsius (° C.) or more to emit electrons, and the electrons are accelerated by an applied electric field and attack the metal target, thereby generating an electromagnetic wave. The thermionic emission tube may have a limitation in that a response time is long because the metal filament has to be heated to a high temperature to emit the electrons.

Meanwhile, a field emission (FE) tube may emit electrons from a negative metal electrode by an applied electric field, but a temperature of an emitter is much lower than a temperature of the filament of the thermionic emission tube. That is, since the negative electrode is lower in temperature than the thermionic emission tube, the field emission tube may have a longer life and a shorter response time. In addition, it is possible to fine-tune a voltage control between electrodes, so it is easy to control an emission of an electromagnetic wave at a desired level. As the field emission tube, a CNT tube using a negative CNT electrode may be used.

Basically, the CNT tube may include an anode of a positive electrode, a cathode of a negative electrode, and a gate for inducing emission of electrons. According to this, a magnitude of voltage of the anode, the cathodes, or the gate may be individually set and learned. Due to the voltages applied to the anode and the cathode, current may flow in the tube, and current may be generated to correspond to a difference in voltage between the anode and the cathode. However, in practice, a high voltage may be applied to the tube to provide a magnetic field enough to eject electrons from the negative electrode, resulting in a leakage current at the gate. Accordingly, the anode, cathode, or gate voltage may be individually controlled to minimize gate leakage current while generating a desired amount of current in the tube.

Figure 4:
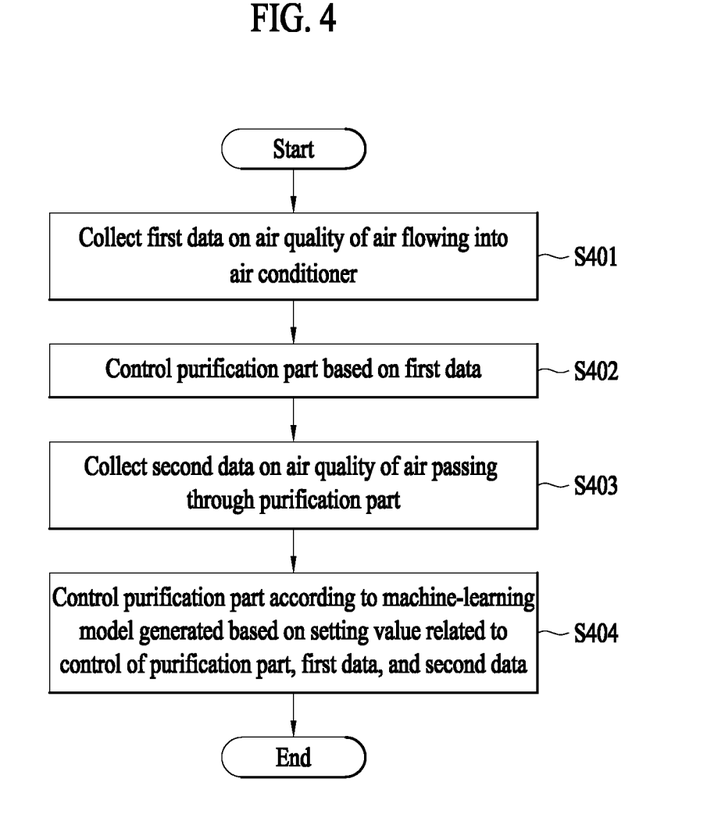
FIG. 4 is a flowchart illustrating a control method of an air handler according to an example embodiment.

FIG. 4 is a flowchart illustrating a control method of an air handler according to an example embodiment.

In operation S401, the method may collect first data on an air quality of air flowing into the air handler. According to an example embodiment, the first data may include at least one of information on air pollutants such as fine dust, VOCs, and formaldehyde, carbon dioxide, a wind speed, a temperature, a humidity, and a size of a space in which the air handler is installed.

In operation S402, the method may control a purification part based on the collected first data. According to an example embodiment, the purification part may include at least one charging part that ionizes at least a portion of substances included in the air and a dust collecting part that collects substances ionized in the charging part. The charging part may ionize the substances using an electromagnetic wave having a wavelength in a range between 0.1 nm and 100 nm, inclusive. Specifically, the charging part may photo-ionize pollutants in the air using extreme ultraviolet or soft X-rays.

In operation S403, the method may collect second data on an air quality of air passing through the purification part.

According to an example embodiment, the second data may include at least one of information on air pollutants such as fine dust, VOCs, and formaldehyde, carbon dioxide, a wind speed, a temperature, a humidity, and a size of a space in which the air handler is installed.

In operation S404, the method may control the purification part according to a machine-learning model generated based on a setting value related to a control of the purification part, the first data, and the second data. According to an example embodiment, the setting value related to the control of the purification part may include setting values for a voltage applied to the charging part and a voltage applied to the dust collecting part. According to an example embodiment, the charging part may include at least one tube that emits an electromagnetic wave. The setting value for the voltage applied to the charging part may include a setting value for a voltage applied to each of a plurality of electrodes included in the tube. Accordingly, machine learning may be individual learning for each of the plurality of electrodes included in the tube. Meanwhile, the method may collect the first data and the second data for a preset period of time in predetermined time units to control the purification part according to the machine-learning model.

To control the purification part according to the machine-learning model, technology of the present disclosure may derive a threshold for a parameter related to an air quality based on the first data and the second data according to the setting value related to the control of the purification part and derive a control condition of the purification part in which the parameter decreases to be less than or equal to the threshold. The control condition of the purification part may include a voltage applied to the charging part and a voltage applied to the dust collecting part. According to an example embodiment, a control condition for the voltage applied to the charging part may include an individual control condition for the voltage applied to each of the plurality of electrodes included in the tube in the charging part. The parameter may include at least one of information on an air pollutant, carbon dioxide, a wind speed, a temperature, a humidity, and a size of a space in which the air handler is installed. The air pollutant may include, for example, one or more air substances harmful to the human body, such as fine dust, VOCs, and formaldehyde. In addition, the threshold may be different for each space in which the air handler is installed and determined based on a size of fine dust included in the second data. For example, different thresholds may be derived from ultrafine dust with a particle size of PM 2.5 and fine dust with a particle size of PM 10.

In relation to the machine learning performed in operation S404, a machine-learning model according to an example embodiment may be generated based on a number of at least one tube that emits an electromagnetic wave in the charging part, a location of the at least one tube, and a size of the dust collecting part as an input value. For this, the method may previously input the input value prior to the machine learning.

According to an example embodiment, the method of the present disclosure may update the machine-learning model based on the first data collected in operation S401 and the second data according to the control condition of the purification part derived in operation S404. For example, the machine-learning model may be continuously corrected based on the first data acquired by sensing the air quality of the air flowing into the purification part and the second data acquired by setting the purification part with the setting value derived through the machine learning and sensing the air quality of the air passing through the purification part.

According to an example embodiment, the machine-learning model may be generated through reinforcement learning in which compensation is performed based on the parameter related to the air quality and power consumption of the purification part. For example, in an environment in which the parameter satisfies the threshold, as the power consumption of the purification part decreases, a larger score may be assigned. Through this, the model may be generated to minimize the power consumption and increase a purification efficiency.

According to an example embodiment, a plurality of air handlers may be installed. In this case, according to different machine-learning models, the respective air handlers may control purification parts therein.

Figure 5:
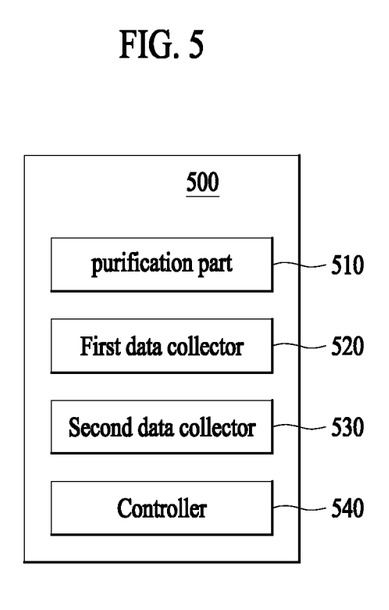
FIG. 5 is a block diagram illustrating an air handler 500 according to an example embodiment.

FIG. 5 is a block diagram illustrating an air handler 500 according to an example embodiment. Referring to FIG. 5, the air handler 500 may include a purification part 510, a first data collector 520, a second data collector 530, and a controller 540.

The first data collector 520 may include at least one sensor and acquire information associated with air flowing into the purification part 510. For example, the first data collector 520 may be located before the purification part 510 and collect first data on an air quality of air before the air passes through the purification part 510. According to an example embodiment, the first data collector 520 may be located before the charging part of the purification part 510 or located after the charging part and before the dust collecting part to sense air. This is a factor that can be changed according to a characteristic of a space where the air handler 500 is installed and the needs of a user of installation.

The second data collector 530 may include at least one sensor and acquire information associated with air discharged from the purification part 510. For example, the second data collector 530 may be located after the purification part 510 and collect second data on an air quality of air passing through the purification part 510.

The purification part 510 may include at least one charging part that ionizes at least a portion of substances included in the air and a dust collecting part that collects ionized substances. By controlling voltages applied to the charging part and the dust collecting part, it is possible to increase an air purification efficiency per power consumption of the air handler 500.

The controller 540 may collect first data on an air quality acquired through the first data collector 520 and control the purification part 510 based on the first data. In addition, through the second data collector 530, the controller 540 may collect second data on an air quality of air passing through the purification part 510. Also, the controller 540 may control the purification part 510 according to a machine-learning model generated based on a setting value related to a control of the purification part 510, the first data, and the second data.

According to an example embodiment, based on the machine-learning model, the controller 540 may derive a threshold for a parameter related to the air quality based on the first data and the second data according to the setting value related to the control of the purification part 510. Also, the controller 540 may derive a control condition of the purification part 510 in which the parameter decreases to be less than or equal to the threshold, thereby controlling the purification part 510. Specifically, the machine-learning model may be generated through reinforcement learning in which compensation is performed based on the parameter related to the air quality and power consumption of the purification part 510. For example, as the power consumption of the purification part 510 decreases while the parameter related to the air quality satisfies the threshold, a larger score may be assigned to the model to perform the reinforcement learning on the model.

In an example, when an air handler to which the machine learning of the present disclosure is not applied operates at a maximum performance, a voltage of 4.8 kV may be applied to the charging part and a voltage of 4.4 kV may be applied to the dust collecting part. In this case, total power consumption may be 20 W and an average fine-dust removal efficiency may be 15%. That is, when a maximum performance operation condition is applied, a fine-dust removal efficiency per power consumption may correspond to 0.75%/W. In contrast, when an air handler to which the machine learning of the present disclosure is applied operates at an optimal performance, a voltage of 4.3 kV may be applied to the charging part and a voltage of 3.5 kV may be applied to the dust collecting part. In this case, total power consumption may be 8 W and an average fine-dust removal efficiency may be 14%. That is, when an optimal performance operation condition is applied, a fine-dust removal efficiency per power consumption may correspond to 1.75%/W, which is higher compared to a case in which the machine learning is not applied. Accordingly, a fine-dust removal performance is not reduced despite the decrease in power consumption, so that the fine-dust removal efficiency per power consumption may be increased.

The air handler 500 of FIG. 5 is merely an example, and may further include other components in addition to the components shown in FIG. 5. Also, the air handler 500 may implement the above-described example embodiments through the components.

The present specification and drawings have been described with respect to the example embodiments of the present disclosure. Although specific terms are used, it is only used in a general sense to easily explain the technical content of the present disclosure and to help the understanding of the invention, and is not intended to limit the scope of the specification. It will be apparent to those skilled in the art that other modifications based on the technical spirit of the present disclosure may be implemented in addition to the embodiments disclosed herein.

What is claimed is:

1. A method of controlling a machine learning-based air handler, the method comprising:
    collecting first data on an air quality of air flowing into the air handler;
    controlling a purification part comprising at least one charging part having at least one tube comprising an anode and a cathode and a dust collecting part that collects ionized substances with a positive charge and a negative charge based on the first data;
    collecting second data on an air quality of air passing through the purification part; and
    controlling the purification part according to a machine-learning model generated based on a setting value related to a control of the purification part, the first data, the second data, and an input value including a number of at least one tube, a location of the at least one tube, and a size of the dust collecting part,
    wherein the setting value related to the control of the purification part comprises at least one of a voltage value applied to the anode and a voltage value applied to the cathode, and
    wherein the at least one charging part ionizes substance by emitting electromagnetic wave having a wavelength in a range between 0.1 nanometers and 100 nanometers using the cathode composed of carbon nanotube.

2. The method of claim 1, wherein the first data and the second data include at least one of information on an air pollutant, carbon dioxide, a wind speed, a temperature, a humidity, and a size of a space in which the air handler is installed.

3. The method of claim 1, wherein the setting value related to the control of the purification part further includes setting value for a voltage applied to the dust collecting part.

4. The method of claim 1, wherein the controlling of the purification part according to the machine-learning model comprises:
    deriving a threshold for a parameter related to an air quality based on the first data and the second data according to the setting value related to the control of the purification part; and
    deriving a control condition of the purification part in which the parameter decreases to be less than or equal to the threshold.

5. The method of claim 4, wherein the parameter includes at least one of information on an air pollutant, carbon dioxide, a wind speed, a temperature, a humidity, and a size of a space in which the air handler is installed.

6. The method of claim 4, wherein the threshold is different for each space in which the air handler is installed and determined based on size information of fine dust included in the second data.

7. The method of claim 4, wherein
the control condition of the purification part includes a voltage applied to the charging part and a voltage applied to the dust collecting part.

8. The method of claim 4, further comprising:
    updating the machine-learning model based on the first data and second data according to the derived control condition of the purification part.

9. The method of claim 1, wherein the controlling of the purification part according to the machine-learning model further comprises:
    collecting the first data and the second data for a preset period of time in predetermined time units.

10. The method of claim 1, wherein the machine-learning model is generated through reinforcement learning in which compensation is performed based on a parameter related to an air quality and power consumption of the purification part.

11. The method of claim 1, wherein each of a plurality of air handlers including the air handler is controlled by different machine-learning models.

12. The method of claim 2, wherein the air pollutant includes at least one of fine dust, volatile organic compounds (VOSs), and formaldehyde.

* * * * *